(12) United States Patent
Holmes et al.

(10) Patent No.: US 6,740,047 B2
(45) Date of Patent: May 25, 2004

(54) MOTILITY ANALYSIS, DISPLAY, AND INTERPRETATION SYSTEM

(76) Inventors: Harlan K. Holmes, 301 Dominion Dr., Newport News, VA (US) 23602; Ray E. Clouse, 320 N. Union Blvd., St. Louis, MO (US) 63108; Domenic A. Bellino, 904 James Ct., Wheaton, IL (US) 60187

( * ) Notice: Subject to any disclaimer, the term of this patent is extended or adjusted under 35 U.S.C. 154(b) by 181 days.

(21) Appl. No.: 10/054,791

(22) Filed: Jan. 25, 2002

(65) Prior Publication Data

US 2003/0144604 A1 Jul. 31, 2003

(51) Int. Cl.[7] .................................................. A61B 5/00
(52) U.S. Cl. ....................... 600/561; 600/480; 600/485; 600/593; 385/12
(58) Field of Search .......................... 128/920, 922–925; 600/300, 480, 485, 561, 585, 593, 587; 385/12

(56) References Cited

U.S. PATENT DOCUMENTS

| | | | | |
|---|---|---|---|---|
| 3,480,003 | A | * 11/1969 | Crites | 600/593 |
| 6,471,656 | B1 | * 10/2002 | Shalman et al. | 600/486 |
| 6,585,660 | B2 | * 7/2003 | Dorando et al. | 600/486 |
| 2002/0138009 | A1 | * 9/2002 | Brockway et al. | 600/485 |
| 2003/0100845 | A1 | * 5/2003 | Eide | 600/561 |

OTHER PUBLICATIONS

Alrakawi, et al., Gastroenterology, 2000: 118: A243.
Clouse, et al., Am. J. Physiology, 261; G677–G684,(1991).
Clouse, et al., Am J. Physiology, 265; G1098–G1107,(1993).
Clouse, et al., Digestive Diseases, vol. 41, No. 12; 2369–2376,(1996).
Clouse, et al., Digestive Diseases, vol. 43, No. 9; 1978–1985,(1998).

* cited by examiner

Primary Examiner—Max F. Hindenburg
Assistant Examiner—Jonathan Foreman
(74) Attorney, Agent, or Firm—George F. Helfrich

(57) ABSTRACT

The system includes an array of transducers that simultaneously senses multiple intralumenal pressures, a data acquisition module that acquires and stores samples of the measured pressures, software routines for signal analysis, a software module for multi-dimensional data display presentations, and a software module to perform pattern recognition on the acquired data set to identify potential maladies that may be indicated by the analysis. The transduction elements are cylindrical segments that deform according to the circumferential pressures encountered. Distributing a quantity of these sensor segments at desired locations along a flexible support structure and providing a flexible sheath over the entire length forms the sensor array. Measuring the sensor deformation provides an electrical analog of the pressure causing the deformation. Acquiring these measurements in a suitable data acquisition and processing unit, including a display, printing, and plotting capability, completes the hardware elements. Integrated software modules complete the system.

6 Claims, 5 Drawing Sheets

MOTILITY ANALYSIS, DISPLAY, AND INTERPRETATION SYSTEM

BACKGROUND OF THE INVENTION

1. Field of the Invention

This invention relates generally to medical diagnostic systems and methods. It relates particularly to a system and method for providing a probabilistic diagnosis of physiological dysfunction present in any of several tubular cavities within a living body.

2. Description of the Related Art

Motility within tubular structures of the body typically is the result of a complex interaction of muscles and their neural control mechanisms. Motility disorders that most commonly reach clinical significance are the motility disorders of the gastrointestinal tract. The prevalence of these disorders is significant, and their diagnosis and management consumes a large amount of health care resources. A variety of methods have been employed to correctly diagnose the nature of motor dysfunction, including radiological, radionuclide, and endoscopic procedures. However, these diagnostic tests only provide qualitative and often crude information ultimately used to establish a proper diagnosis of motor dysfunction. Their focus primarily is on evaluation of bolus transit or the luminal surface, excluding structural lesions that may produce clinical presentations mimicking motor disorders.

Intraluminal manometry is a very sensitive method of detecting motor dysfunction and has become the diagnostic gold standard in some parts of the gastrointestinal tract. Pressure measurements have the capability of determining fine errors in motor control before gross alterations in transit are apparent by other testing methods. Likewise, the quantitative outcomes of pressure measurements potentially can classify the type of dysmotility, even when the measured defect is minor. This can lead to earlier interventions and more appropriate treatments. Despite the appeal of intraluminal manometry, currently available systems have important limitations. The most important of these is that few recording sensors are used, the sensors are spaced such that spatial resolution is inadequate, and the resultant methods of analysis are inconsistent because of lack of sufficient data.

Intraluminal manometry is accomplished either by use of electromechanical systems with transduction (recording) devices embedded in intraluminal probes or water-perfused systems with the intraluminal catheter attached to extracorporeal transducers. In the former systems, current intraluminal probes typically include no more than 4 sensors, severely limiting the amount of acquired pressure information. For example, the esophagus, the most commonly studied gastrointestinal organ for its motor function, is more than 20 cm long within its body, and several centimeters of sphincter are found at each end. Best approximation of the peristaltic wave of motility requires sampling at 1-cm intervals. Consequently, the present devices are considerably inadequate. To completely characterize the peristaltic wave, from pharyngoesophageal region through the lower esophageal sphincter in all adult subjects, at least 30 sensors recording pressures simultaneously from an intraluminal probe are required. A system of this type presently is not available.

Commercial water-perfused systems are available with more recording sites than the electromechanical systems. The most advanced of these presently allows for 21 recording sites within a probe diameter tolerated by adult subjects for esophageal instrumentation. Consequently, even with this system, only a portion of the esophagus and one bordering sphincter can be studied simultaneously. Water-perfused systems with fewer recording sites are in common use because of their lesser expense than electromechanical devices. However, the demonstration of motor dysfunction is expectedly limited. Water-perfused systems also suffer the limitations imposed by their sensitivity to gravity bias and the important technical burdens in maintaining the perfused catheters and pneumohydraulic pump apparatus. The system requires meticulous cleaning and maintenance to provide accurate pressure data from repeated use, and the apparatus is cumbersome and poorly transportable.

The electromechanical systems generally employ a miniature silicon diaphragm which has a very limited circumferential extent, and which incorporates a piezo-resistive bridge network as a sensor of the diaphragm deformation resulting from the external pressures encountered. Because of the limited circumferential extent, information regarding the luminar pressures at a location may be incomplete. Additionally, electrical conductors must extend through the catheter system to each sensor element, creating a potential safety issue, as well as limiting the number of sensor elements because of the finite space available to route the many conductors through the central catheter lumen. In the water-perfused system, small tubes, one for each sensed location, must be contained in a larger lumen, and each tube terminated at the sensed location by a hole in the outer lumen wall. This hole is also of a very limited circumferential extent, and a large number of sensor locations require an increasing diameter of the outer lumen. This ultimately limits the practical number of sensors that can be accommodated. The fluid path(s) also present an electrically conductive path, which also contributes to safety concerns.

Requirements for the spatial density of recording sensors will undoubtedly vary across tubular organs in the body. Presently, the gastrointestinal tract is an important organ system with clinically relevant motility disorders, and, within that system, the most studied tubular organ for its motor function is the esophagus. Through a series of reports from 1991–2000, Clouse demonstrated that complete characterization of the esophageal peristaltic sequence would require 1-cm sensor spacing; including appropriate oropharyngeal and gastric sensors to fulfill measurement requirements, thirty-two simultaneous intraluminal pressure measurement are needed. Adding a requirement that the sensors have sensitivity to pressures over a significant circumferential extent would improve the completeness of the measurement at each sensor location. Employing fiber-optic techniques to sense the deformation of the segment would eliminate any electrical safety concern, as no electrically conductive path would exist.

Modern desktop computers can acquire, store and process large quantities of data obtained from multivariate sources and acquisition of data from sixty-four data channels with sixteen-bit resolution and at speeds greater than 100 kilosamples per second is possible today. Processor speeds approaching a billion operations per second, on-board storage of several hundred million bytes of information, and high speed mass storage devices capable if tens of billion bytes of information are now in existence. With these capabilities, very sophisticated signal processing operations such as data averaging, filtering and engineering unit conversion can be accomplished in virtually real-time. Elaborate graphical displays of multivariate data—"waterfall diagrams", "mesh diagrams", "contour plots", and "contour plots employing "pseudo-colors"—are encountered in many fields, computational fluid dynamics, seismology, and target identification and tracking to name a few. Of relevance to this disclosure is display of the space-time-amplitude distribution of the bodily pressures being exerted along any of several tubular cavities within the body. Classification of the medical conditions implicit in these complex sets of data has been performed by experts in the field who have access to systems that can acquire the requisite data. At the present time, interpretation of a given set of data may result in inconsistencies because of different medical training, experience, stress level, etc.; or one physician's mental rules may be difficult to articulate and thus difficult to transfer to others; or where the patient's condition is overly complex and not well understood. Some of these inconsistencies may be eliminated or reduced through the application of computer aided diagnostic routines based on some form of artificial intelligence (AI) technology. In this context, AI is deemed to be the use of advanced computing techniques for performing tasks usually considered to require human insight or intervention. AI includes many advanced computational techniques including expert systems, artificial neural networks, fuzzy logic, and genetic algorithms. Expert systems are rule-based systems where the rules are based on expert decisions or on historical data. One usually describes these routines as a compilation of IF-THEN statements. Fuzzy logic allows for some relaxation of the rules by defining a percentage membership in a set. In genetic algorithms, varying each of a problem's parameters over the allowable ranges generates a population of random potential solutions. An "objective" function then rates each member of the population. New individuals are then generated by combining the parameters of two random members of the population (mixing genes) or by randomly varying one or more parametric values of an existing population member (mutation). When a new member is generated, it is compared with the weakest member of the population. If it is stronger than the weakest member, it assumes a place in the population and the weakest member is discarded. The process continues until little further improvement is noted. The fittest member is then regarded as the optimized solution. Artificial neural networks are self-optimizing predictive programs that are useful when historical data on system performance is available. Unlike expert systems, where predictive or analytical rules are usually derived explicitly, neural networks learn through repeated examination of sample cases. Data is presented to a network-training program in the form of training sets, which consist of input data (such as the result of a set of medical tests) and output or results (a validated diagnosis of the patient's condition). When the network has completed its training on the supplied historic data, it can be used to predict cases upon which it has not been trained, provided the situation to be predicted is reasonably similar to the training cases.

SUMMARY OF THE INVENTION

It is the primary object of this invention to provide a system and method that acquires, graphically displays, and analytically interprets the space-time pressure distributions within a bodily cavity or lumen. To achieve this objective, the system includes: (1) a catheter made up of a flexible support structure with multiple transducer segments, each sensitive to externally applied, circumferential pressures, discretely located along its length; (2) a signal conditioning sub-system to provide an electrical analog of the applied pressure from each measuring segment; (3) a data acquisition unit where the raw analog data from each segment is acquired, normalized, converted to engineering units, and stored so that further data processing might be performed; (4) any of several data processing routines such as averaging, windowing, correlation analysis, and the like; (5) a data plotting module where various data visualization presentations are constructed, such as amplitude vs. time plots for discrete segments, 3-D mesh or waterfall plots to visualize the amplitude-space-time relationships, and/or space-time relationships with amplitude expressed by contours or pseudocolor; (6) and finally, an interpretive module that, once trained, identifies the most probable dysfunction characterized by that data set.

Up to the present time, clinical studies alluded to herein have been conducted by experts in facilities conducting research or in facilities specializing in a particular physiological dysfunction, which obviated the need for more inclusive systems. Multiple sensors to adequately characterize the bodily structure of interest from a single forcing function and sufficiently powerful desk top computer systems and data acquisition capabilities to acquire, process and display the acquired data sequence in near real-time are now available. Adding built-in diagnostic routines to interpret the acquired data patterns and identify the most probable dysfunction, allows the present system to be utilized by less skilled practitioners. Obtaining, displaying, and interpreting a sufficiency of data in a minimum of time will minimize the discomfort to the patient, reduce the cost of patient care, and greatly increase the number of facilities where comparable investigations can be performed. Also, because the data is now in a standardized form, it is easily transmitted electronically to a specialist for additional consultation.

BRIEF DESCRIPTION OF THE DRAWINGS

For a more complete understanding of the present invention, including its primary object and attending benefits, reference should be made to the Detailed Description of the Invention, as set forth below. This Detailed Description should be read together with the accompanying drawings, wherein.

DETAILED DESCRIPTION OF THE INVENTION

Figure 1:
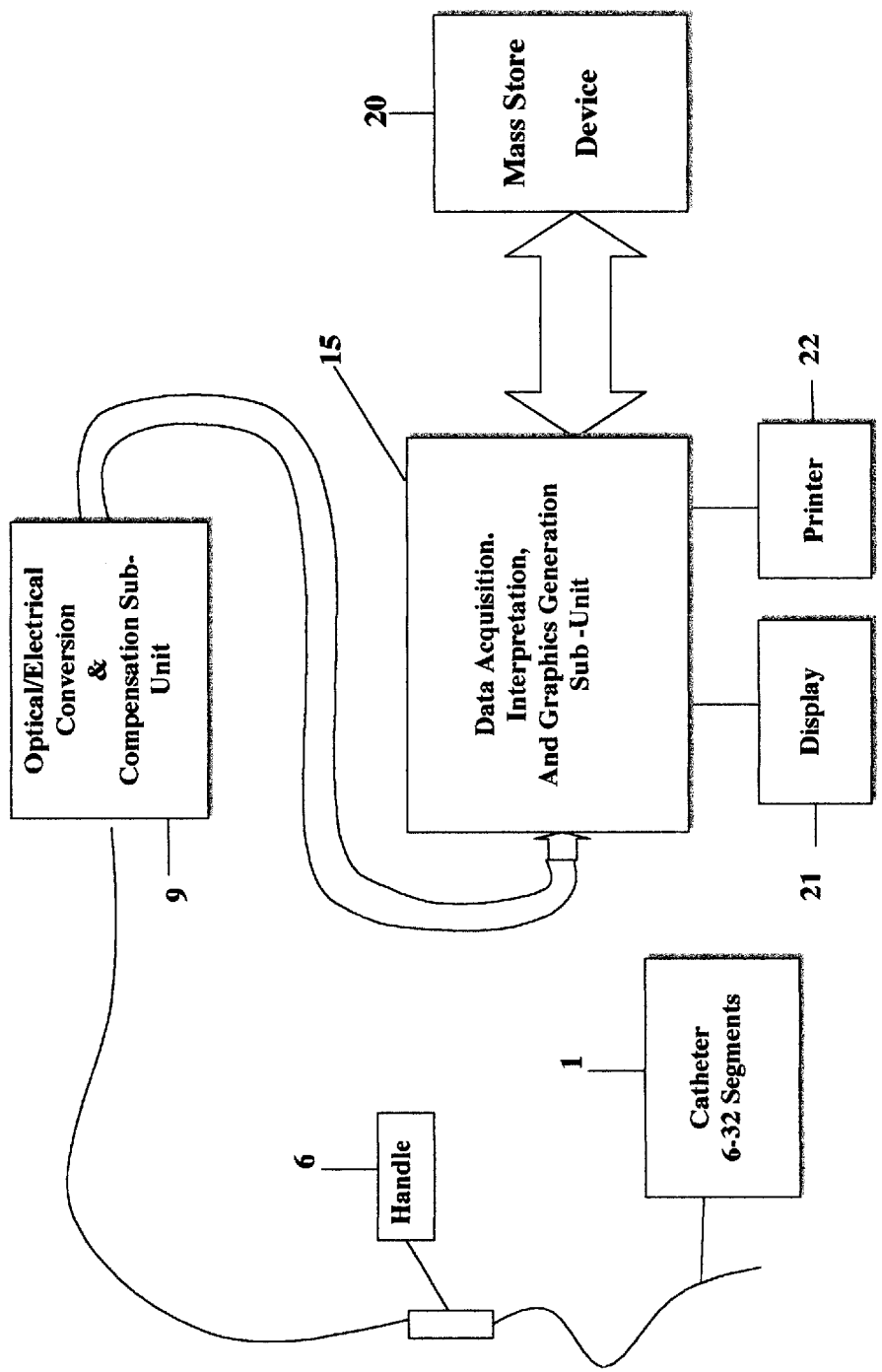
FIG. 1 is an overall schematic depicting the system according to the present invention.
Figure 2:
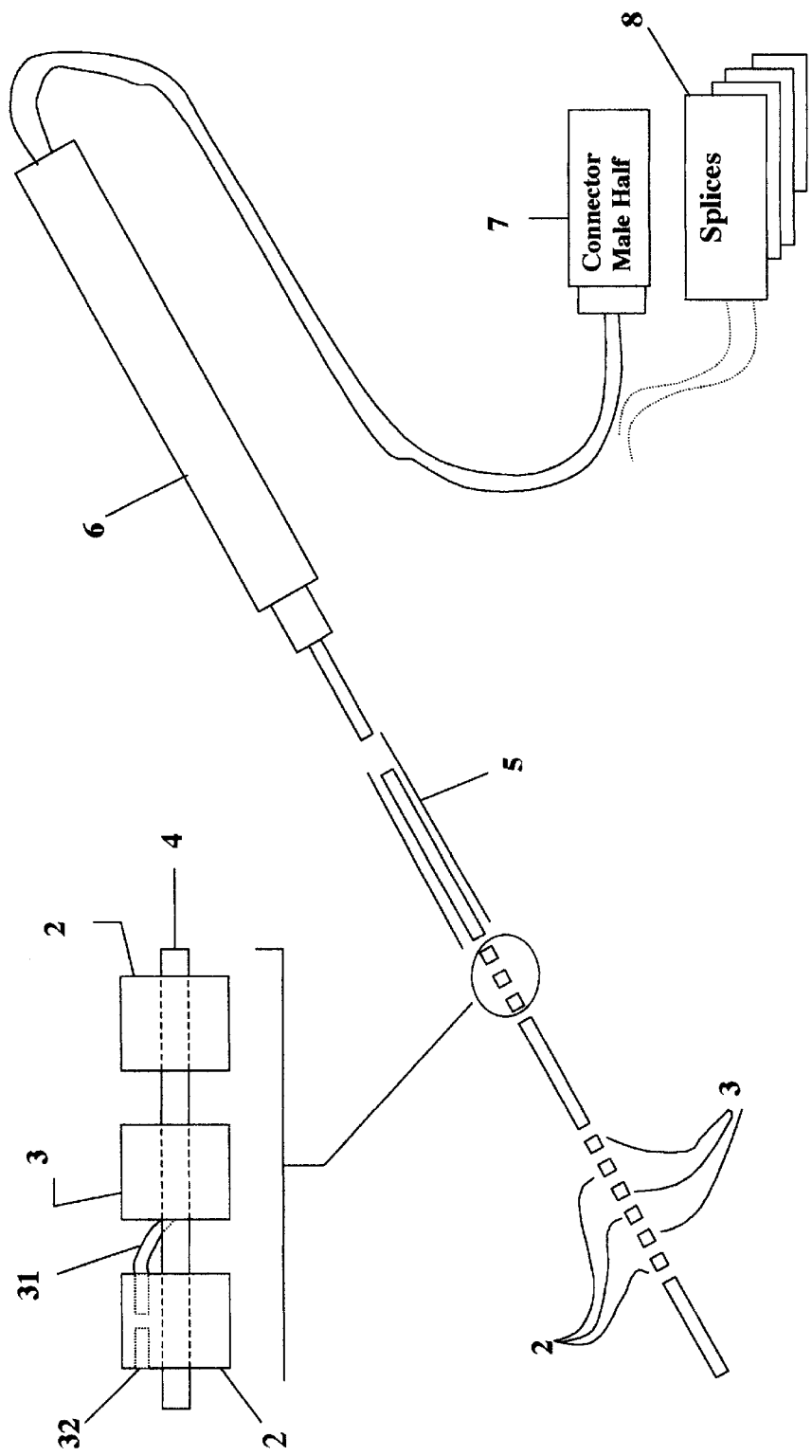
FIG. 2 is a schematic depicting the catheter sub-unit of the system according to the present invention.
Figure 3:
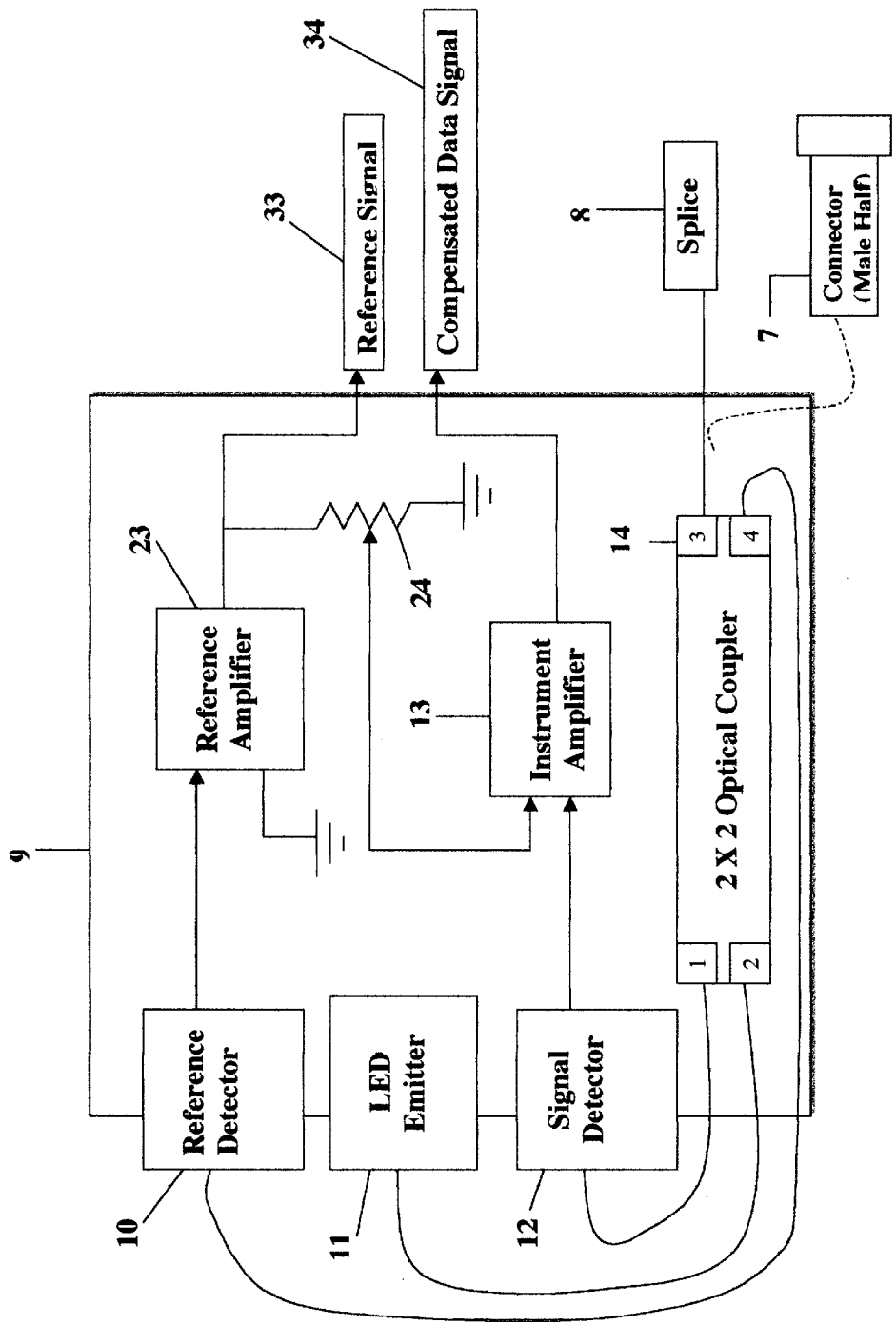
FIG. 3 is a schematic depicting the signal-conditioning sub-unit of the system according to the present invention.

Referring now to the drawings, an overall depiction of a preferred embodiment, consisting of sub-units and modules, is represented in FIG. 1, which shows the spatial array of opto-mechanical transducer elements, 1; the electro-optical analog conversion and optical power compensation sub-unit, 9; the multiple channel data acquisition, data scaling, and engineering unit conversion sub-unit, 15; the data and program storage unit, 20, system display, 21, and system printer, 22. FIG. 2 details the catheter sub-unit, 1, where an array of 6 to 32 circumferentially sensitive pressure measuring segments, 2, are arranged from the near distal to near proximal end, either uniformly or non-uniformly spaced to optimize a regional spatial resolution, and thence to a handle, 6, which provides a convenient handling and reference point. Shown also are the spacers, 3, and the surrounding sheath, 5. The expanded view of a portion of the catheter shows the arrangement of the optical fiber, 31, its relation to the mirror, 32, in a measuring segment, and the structural spine, 4, which extends from the handle, 6, to the distal tip of the catheter. From the handle, 6, a convenient distance is provided to locate the optical fiber connector 7, or a mechanical splice, 8 and subsequent data acquisition and processing systems. FIG. 3 depicts the optical to electrical conversion and compensation sub-unit containing, for each measuring segment, the optical light source, 11, a 2×2 optical coupler, 14, the pressure modulated optical return signal detector, 12, the reference optical signal detector, 10, the reference signal amplifier, 23, the signal balancing potentiometer, 24, and the combining of these signals in an instrument amplifier, 13, to provide an analog voltage proportional to the modulated pressure signal and compensated for any variation in optical source strength. Light from the light-emitting-diode light source, 11, enters the 2×2 optical coupler, 14, via port 1 and is split equally between two output ports, 3 and 4 respectively. Light leaving port 3 is directed through one pin of the optical-fiber connector, 7, or splice, 8, and propagates through the optical fiber, 31, to the measuring segment, 2, where it is reflected by a mirror, 32, within the segment. The reflected light then retraces the fiber through the connector, 7, or splice, 8, and re-enters the coupler via port 3. In traversing the coupler, the returning light is again divided equally between ports 1 and 2 with light emanating from port 2 being directed to the optical signal detector, 12. Here it is converted to an electrical signal, modulated according to the amount of light being reflected from the mirror, 32, in the measuring segment, 2. Light emanating from port 4 of the coupler is directed to a second optical detector, 10, which creates a reference electrical signal that is then amplified in the reference amplifier, 23, and scaled by potentiometer, 24, and then combined with the modulated electrical signal in the differential instrument amplifier, 13. The output of the instrument amplifier, 13, is an analog voltage proportional to the pressure encountered by the measuring segment, 2, which has been compensated for changes in the optical source strength. Reference signal, 33, and the compensated data signal, 34, are now Reference signal, 33, and the compensated data signal, 34, are now available to be sampled in the analog data input multiplexer, 35, and then acquired by the data acquisition module, 16.

Figure 4:
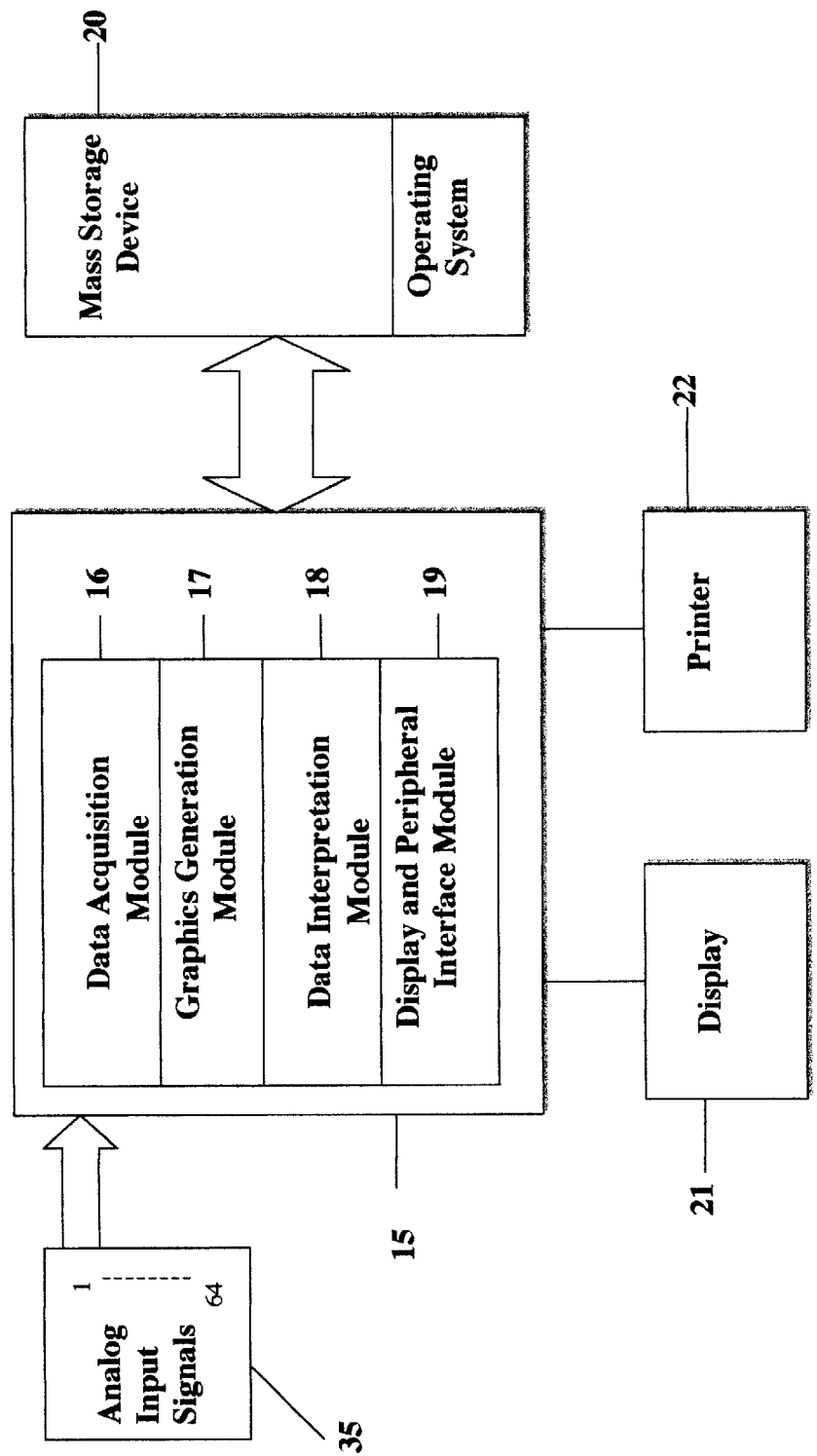
FIG. 4 is a schematic depicting the data acquisition, storage, graphics display and interpretation module of the system according to the present invention.

FIG. 4 is a representative schematic of the data acquisition, graphics generation, and data interpretation sub-unit, 15. This sub-unit is basically a single or multi-processor stored program computer which contains the requisite control of peripherals, 19, that acquires, 16, displays, 21, prints or plots, 22, any visual or hard copy output communication, and stores, 20, the data and program modules. Many data acquisition capabilities are available ranging from 4 to 64 data channels on a single board. As shown, a 64-channel module is being used for an esophageal application, however, other requirements, i.e. fewer channels or higher sampling speeds, might dictate other units. Once the data is acquired, a large variety of data processing functions can be invoked and then the graphics generation module, 17, generates selected display formats to best present the information. A printed hard copy of the information displayed is also an option. An artificial intelligence neural network data interpretation module, 18, can be invoked which normalizes the data set so that data set comparisons can be made and then provides the most probable malady, given that adequate training of the module has been accomplished in order to recognize or predict the most likely outcome.

Figure 5:
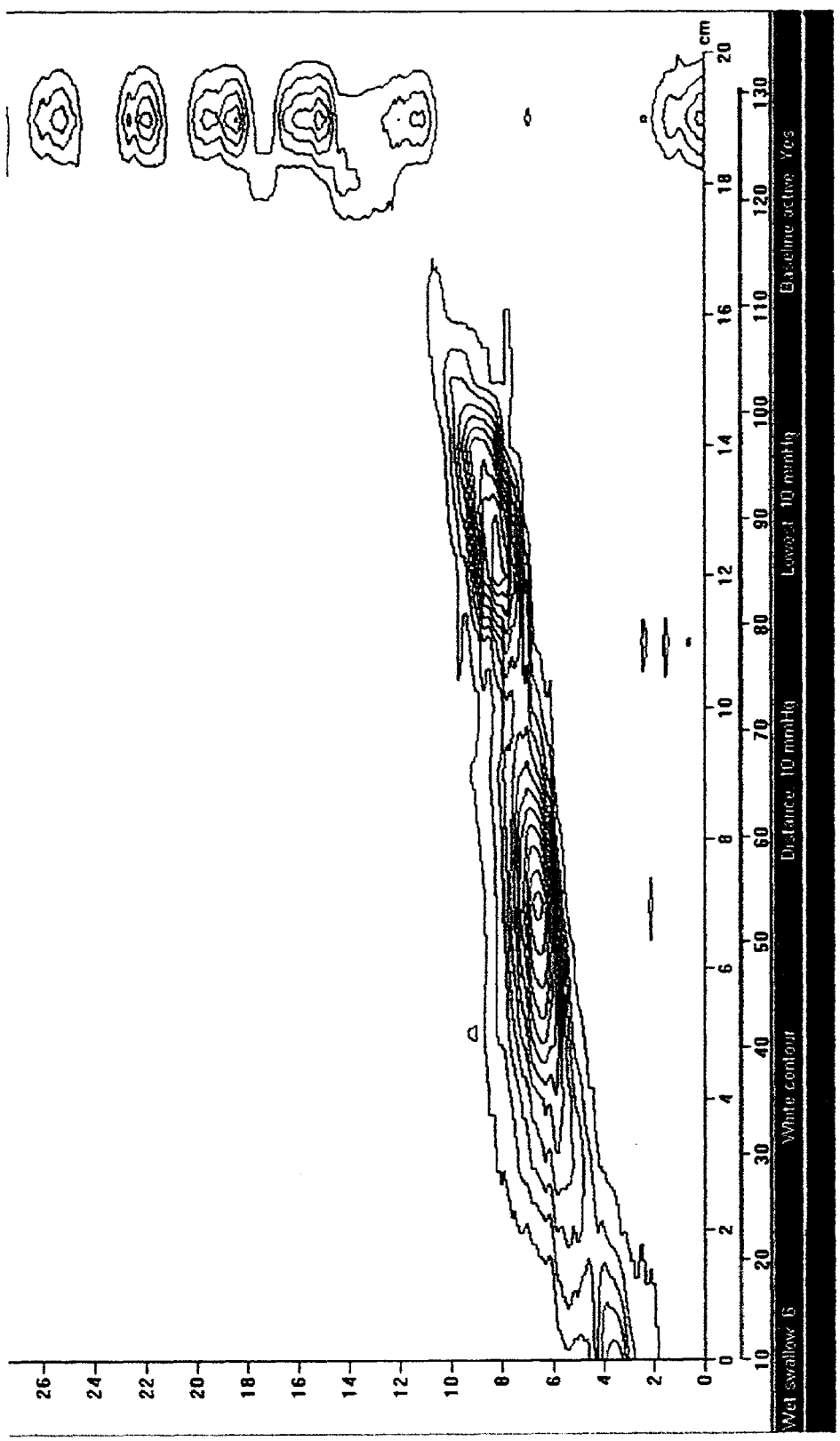
FIG. 5 is a typical display graphic obtained by the system according to the present invention.

FIG. 5 illustrates one type of graphical output, the contour plot representation. In this presentation, space and time are the coordinate axis with pressures represented by contours of equal pressures. This same display is often seen, where color capabilities exist, with pressures expressed in pseudo-colors. It should be noted that only 21 spatial locations are shown in FIG. 5, illustrating the more distal portions of the esophagus. This emphasizes the need for 32 measurements to characterize the response of the entire length of the esophagus during the same input forcing function. A second, frequently encountered, form of the display seen in FIG. 5, is the "water fall" or mesh diagram where amplitude vs. space and time is presented in a pseudo 3-D format. Other displays, e.g. amplitude vs. time for one or a few spatial locations might also be of interest because a greater level of detail can be more easily discerned.

One skilled in the art will recognize that the present invention can be varied in many ways. Though diagnosis of the esophagus is the principal end use described herein, other tubular cavities within the body can be studied in a similar fashion with a possible modification as to the

We claim:

1. A system for providing a probabilistic diagnosis of physiological dysfunction present in a tubular cavity within a living body, comprising:
   a catheter for obtaining circumferential pressure measurements at discrete locations along the body of the catheter and presenting analog representations of the circumferential pressure measurements;
   means for acquiring the analog representations and storing them to make them available for processing;
   means communicating with the means for acquiring the analog representations for generating descriptive graphical displays to facilitate visualization of physiological phenomena; and
   means communicating with the means for processing the analog representations and communicating with the means for generating descriptive graphical displays for interpreting physiological data obtained from within the tubular cavity within the living body and providing a probabilistic diagnosis based on the physiological data,
   wherein the catheter comprises a plurality of measuring segments, each measuring segment being maximally responsive to encountered circumferential pressure, each measuring segment communicating with signal conditioning circuitry by means of an optical fiber, wherein light is transmitted to the measuring segment from a light source at the proximal end of the optical fiber to a mirror assembly located in the segment and positioned opposite the optical fiber at the distal end of the optical fiber, so that encountered circumferential pressure deforms the segment, causing a misalignment of the position of the mirror assembly vis-a-vis the distal end of the optical fiber, resulting in a modulation of reflected light strength.

2. The system of claim 1, wherein the light source at the proximal end of the optical fiber is coupled to a 2×2 optical coupler, so that emitted light is split equally, half thereof being sensed by a reference detector and half thereof being directed toward the distal end of the optical fiber where it is modulated by encountered circumferential pressure and reflected back to the optical coupler where it is again split in half, one half being optically coupled to a signal detector and the output combined with the reference signal in an instrument amplifier where output is a replica of the modulated signal compensated for variations in emitted power.

3. The system of claim 1, wherein the means for acquiring the analog representations and storing them to make them available for processing provides for analog output of a plurality of signal channels to be sampled, with samples being stored in a mass storage device for subsequent availability for processing.

4. The system of claim 1, wherein the means for processing the analog representations is a central processing unit, where stored data is scaled, and is subjected to engineering unit conversion and signal processing routines.

5. The system of claim 1, wherein the means for generating descriptive graphical displays is a graphics generation program, wherein acquired data is presented in a graphical format providing a space-time-amplitude description of a studied event.

6. The system of claim 1, wherein the means for interpreting physiological data is a system program routine, which provides interpretation of data received and presents a most probable descriptor of any malady present.

* * * * *